(12) United States Patent
Hovis et al.

(10) Patent No.: US 10,345,290 B2
(45) Date of Patent: *Jul. 9, 2019

(54) ADJUSTABLE BILAYER CAPACITANCE STRUCTURE FOR BIOMEDICAL DEVICES

(71) Applicant: Genia Technologies, Inc., Santa Clara, CA (US)

(72) Inventors: Jennifer Hovis, Mountain View, CA (US); Hui Tian, Cupertino, CA (US); Roger J. A. Chen, Saratoga, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/021,664

(22) Filed: Jun. 28, 2018

(65) Prior Publication Data

US 2019/0004028 A1  Jan. 3, 2019

Related U.S. Application Data

(63) Continuation of application No. 14/606,632, filed on Jan. 27, 2015, now Pat. No. 10,036,739.

(51) Int. Cl.
*G01N 33/487* (2006.01)

(52) U.S. Cl.
CPC .............................. *G01N 33/48721* (2013.01)

(58) Field of Classification Search
None
See application file for complete search history.

(56) References Cited

U.S. PATENT DOCUMENTS

| | | | |
|---|---|---|---|
| 7,217,520 B2 | 5/2007 | Tsinberg | |
| 7,833,396 B2 | 11/2010 | Fukushima | |
| 10,036,739 B2 * | 7/2018 | Hovis | G01N 33/48721 |
| 2004/0022677 A1 | 2/2004 | Wohlstadter | |
| 2005/0079598 A1 | 4/2005 | Davis | |
| 2006/0231419 A1 | 10/2006 | Barth | |
| 2007/0105089 A1 | 5/2007 | Deutsch | |
| 2008/0237674 A1 | 10/2008 | Ueda | |
| 2009/0140799 A1 | 6/2009 | Kasperkovitz | |
| 2009/0199960 A1 | 8/2009 | Nuzzo | |
| 2010/0331194 A1 | 12/2010 | Turner | |
| 2013/0087467 A1 | 4/2013 | Yang | |
| 2013/0115137 A1 | 5/2013 | Tao | |

(Continued)

FOREIGN PATENT DOCUMENTS

| | | |
|---|---|---|
| EP | 1712891 | 10/2006 |
| WO | WO-2013063126 | 5/2013 |

(Continued)

*Primary Examiner* — Jermele M Hollington
*Assistant Examiner* — Suresh K Rajaputra
(74) *Attorney, Agent, or Firm* — Genia Technologies, Inc.

(57) ABSTRACT

A nanopore sequencing device is disclosed. The nanopore sequencing device includes a working electrode. It further includes a dielectric layer, wherein a portion of the dielectric layer is disposed horizontally adjacent to the working electrode and a portion of the dielectric layer is disposed above and covering a portion of the working electrode, and wherein the dielectric layer forms a well having an opening above an uncovered portion of the working electrode. A base surface area of the working electrode is greater than a base surface area of the opening above the uncovered portion of the working electrode.

20 Claims, 14 Drawing Sheets

(56) References Cited

U.S. PATENT DOCUMENTS

| | | |
|---|---|---|
| 2013/0325096 A1 | 12/2013 | Dupelle |
| 2013/0325380 A1 | 12/2013 | Behnke, II |
| 2014/0034497 A1 | 2/2014 | Davis |
| 2014/0183667 A1 | 7/2014 | Chang |
| 2014/0329693 A1 | 11/2014 | Reid |

FOREIGN PATENT DOCUMENTS

| | | |
|---|---|---|
| WO | WO-2013123450 | 8/2013 |
| WO | WO-2013191793 | 12/2013 |
| WO | WO-2015057324 | 4/2015 |
| WO | WO-2015061510 | 4/2015 |
| WO | WO-2016122797 | 8/2016 |

* cited by examiner

Dielectric 1

M6

Step A

Dielectric 1 | Dielectric 1

M6

Step B

Dielectric 1 | Metal or metal oxide | Dielectric 1

M6

Step C

Dielectric 2

Dielectric 1 | Working Electrode | Dielectric 1

M6

Step D

Diameter of well

Dielectric 2 | well | Dielectric 2

Dielectric 1 | Diameter of WE | Dielectric 1

M6

Step E

FIG. 13

ADJUSTABLE BILAYER CAPACITANCE STRUCTURE FOR BIOMEDICAL DEVICES

CROSS REFERENCE TO OTHER APPLICATIONS

This application is a continuation of co-pending U.S. patent application Ser. No. 14/606,632 entitled ADJUSTABLE BILAYER CAPACITANCE STRUCTURE FOR BIOMEDICAL DEVICES filed Jan. 27, 2015 which is incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 13 illustrates an embodiment of a process for constructing a cell in a nanopore based sequencing chip, wherein the capacitances $C_{membrane}$ and $C_{dl}$ in the cell may be adjusted independently by adjusting the base surface area of the membrane and the base surface area of the working electrode separately.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
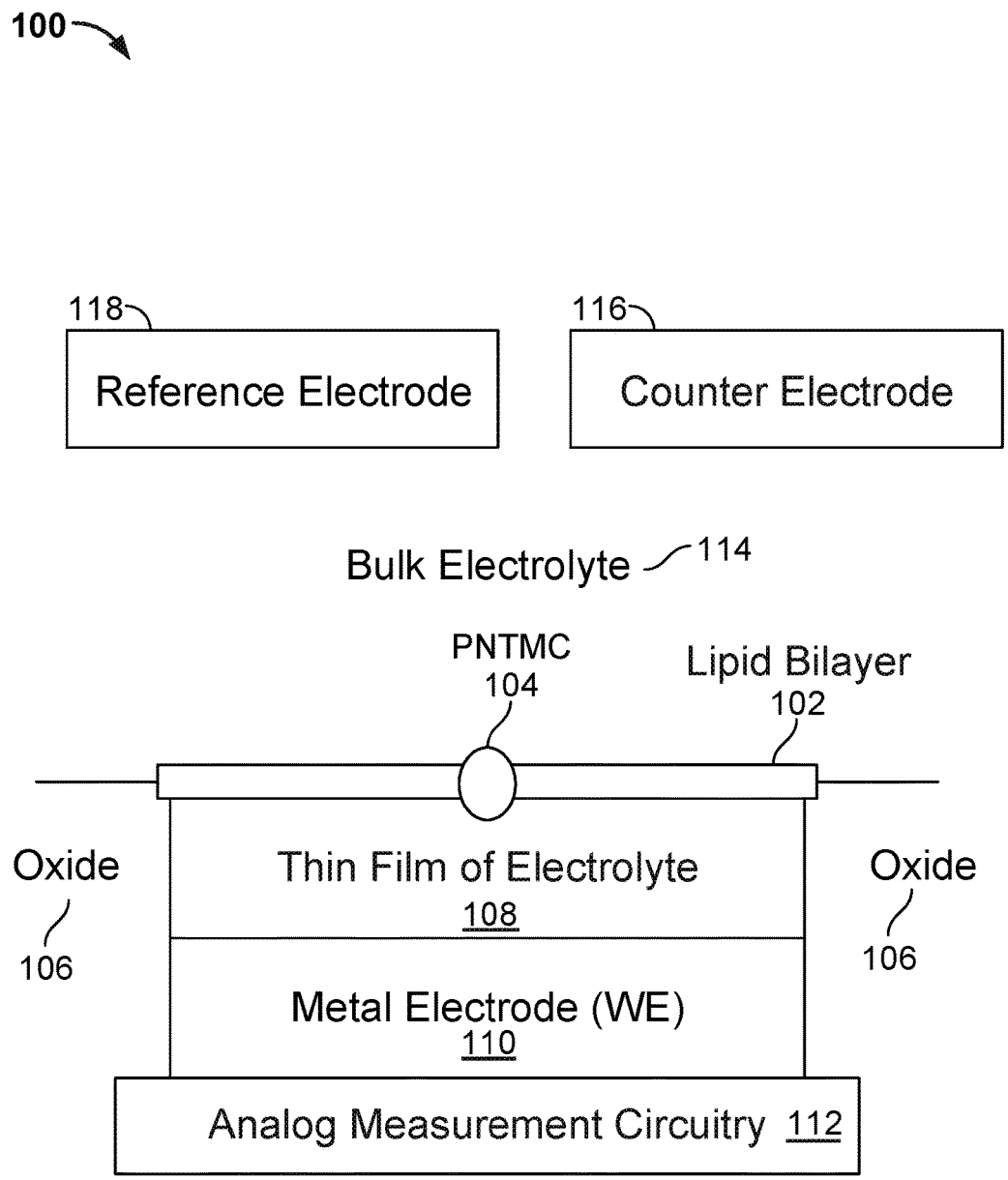
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
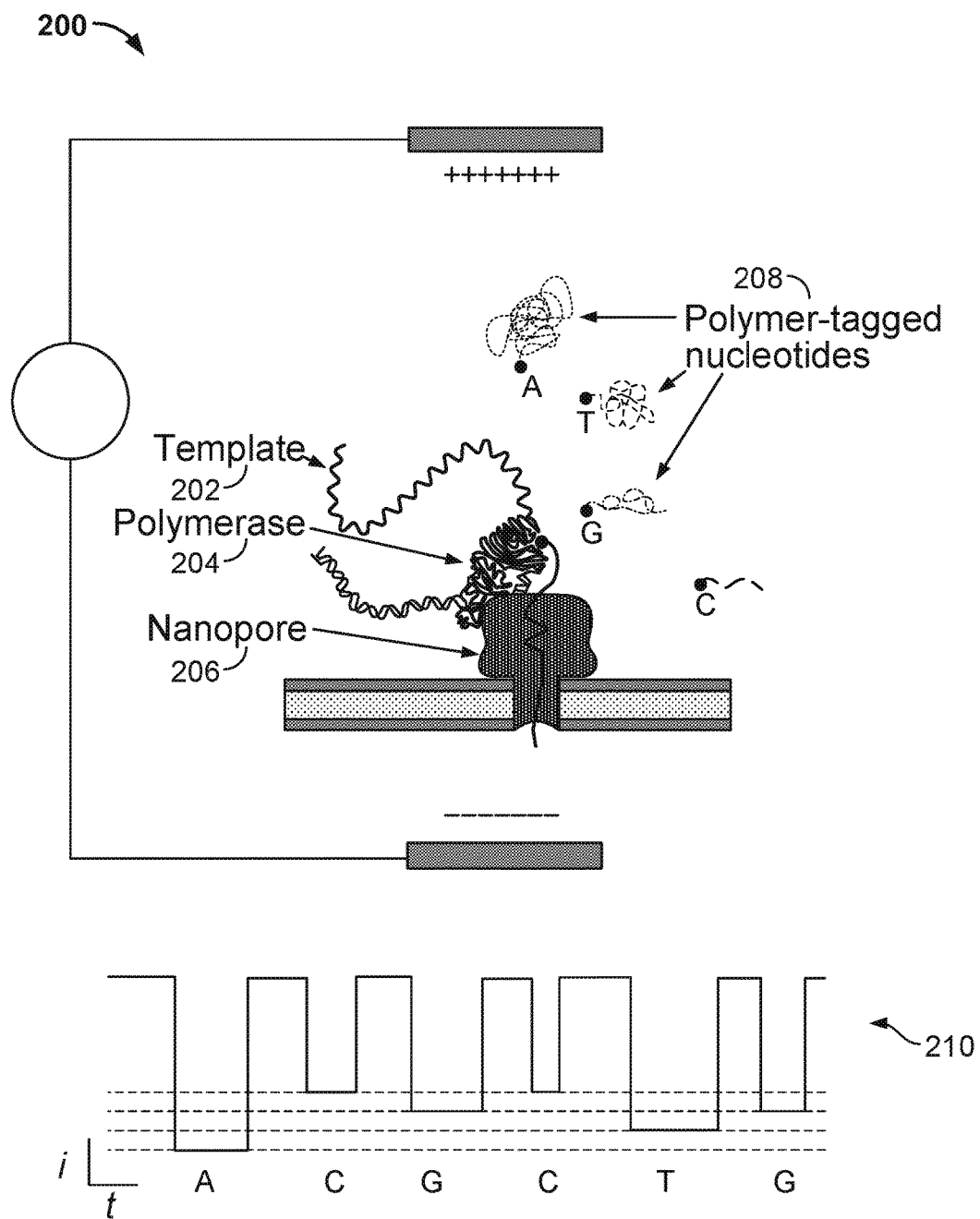
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
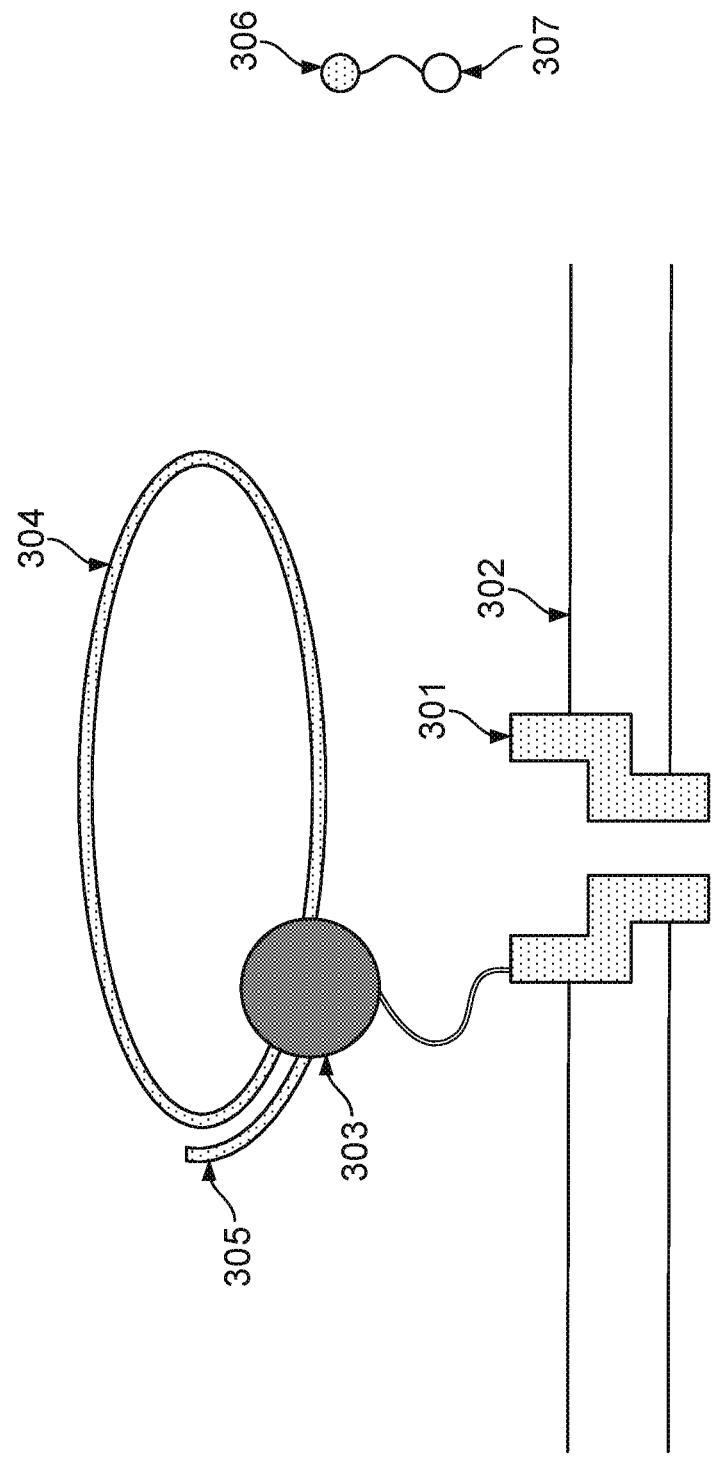
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
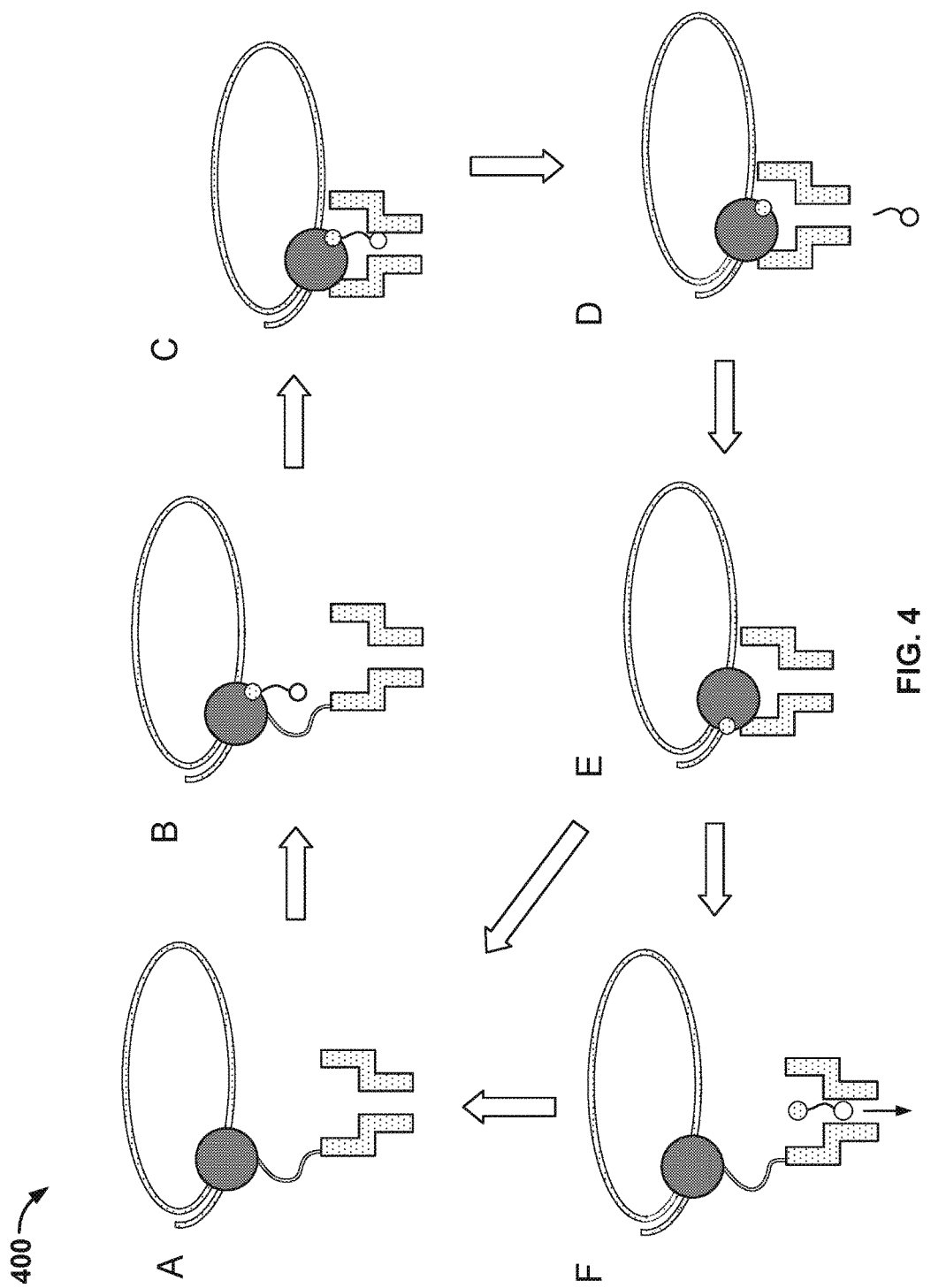
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
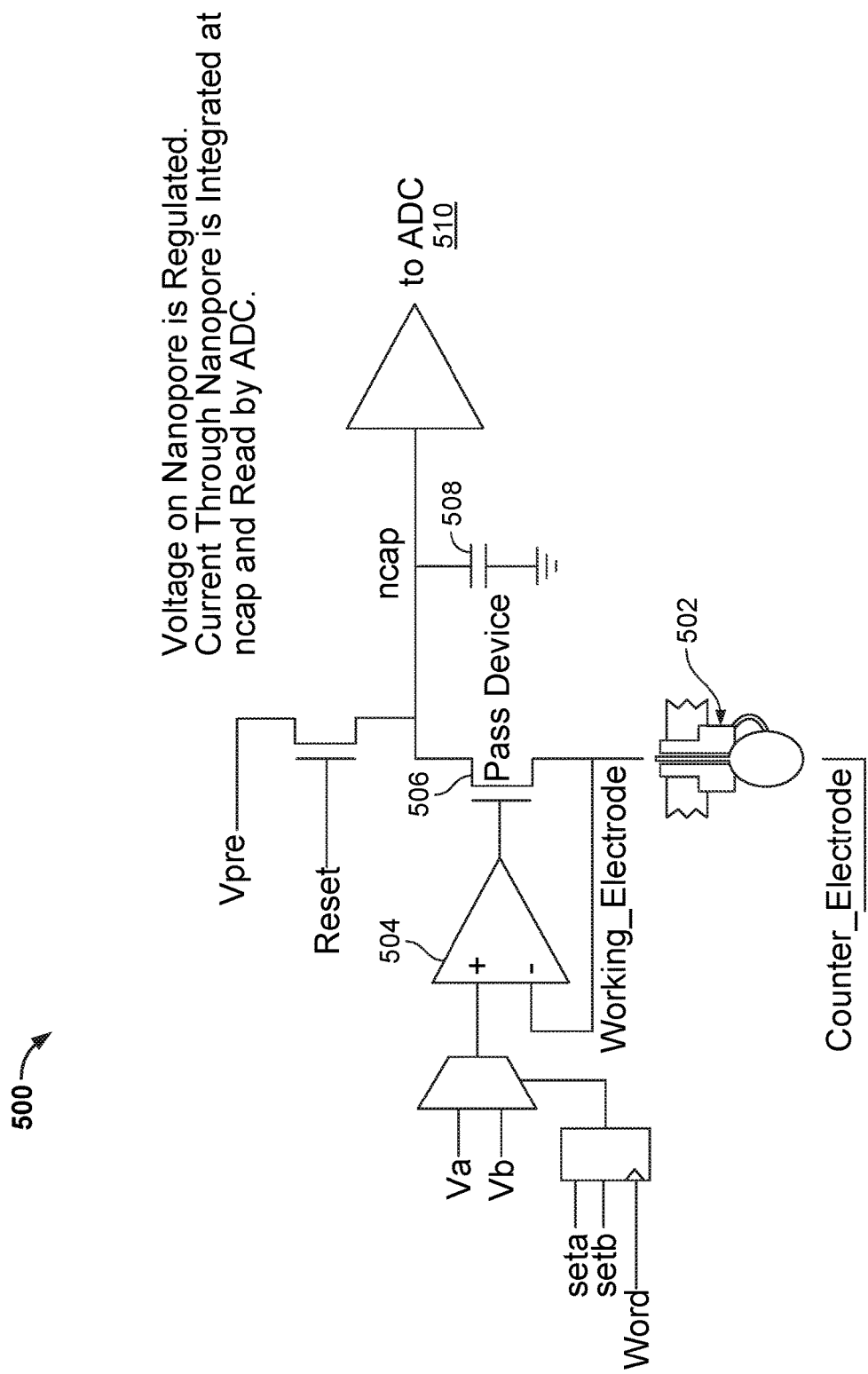
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues. For example, it may exacerbate the offset and noise problems in the cells even further.

Figure 6:
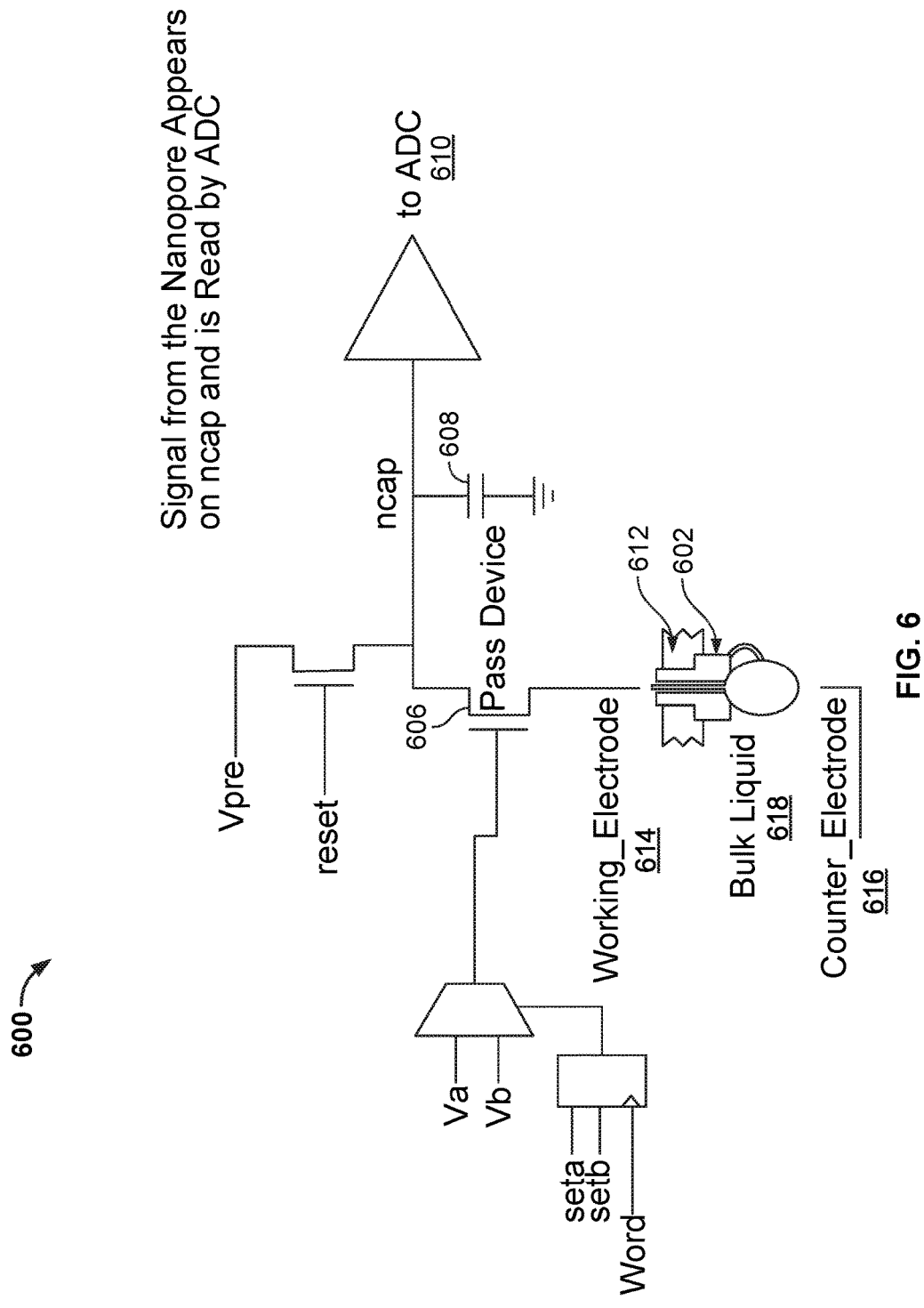
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
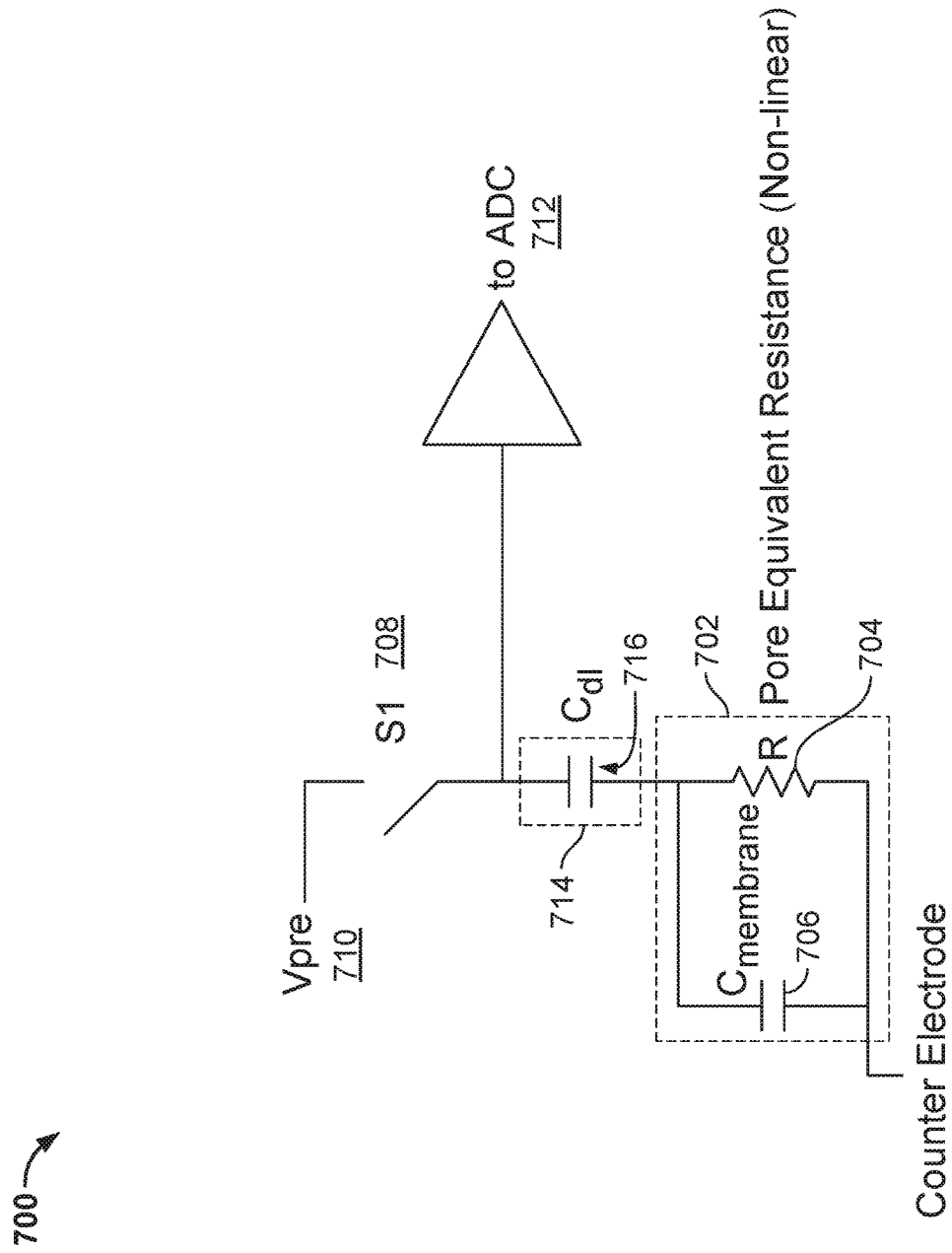
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
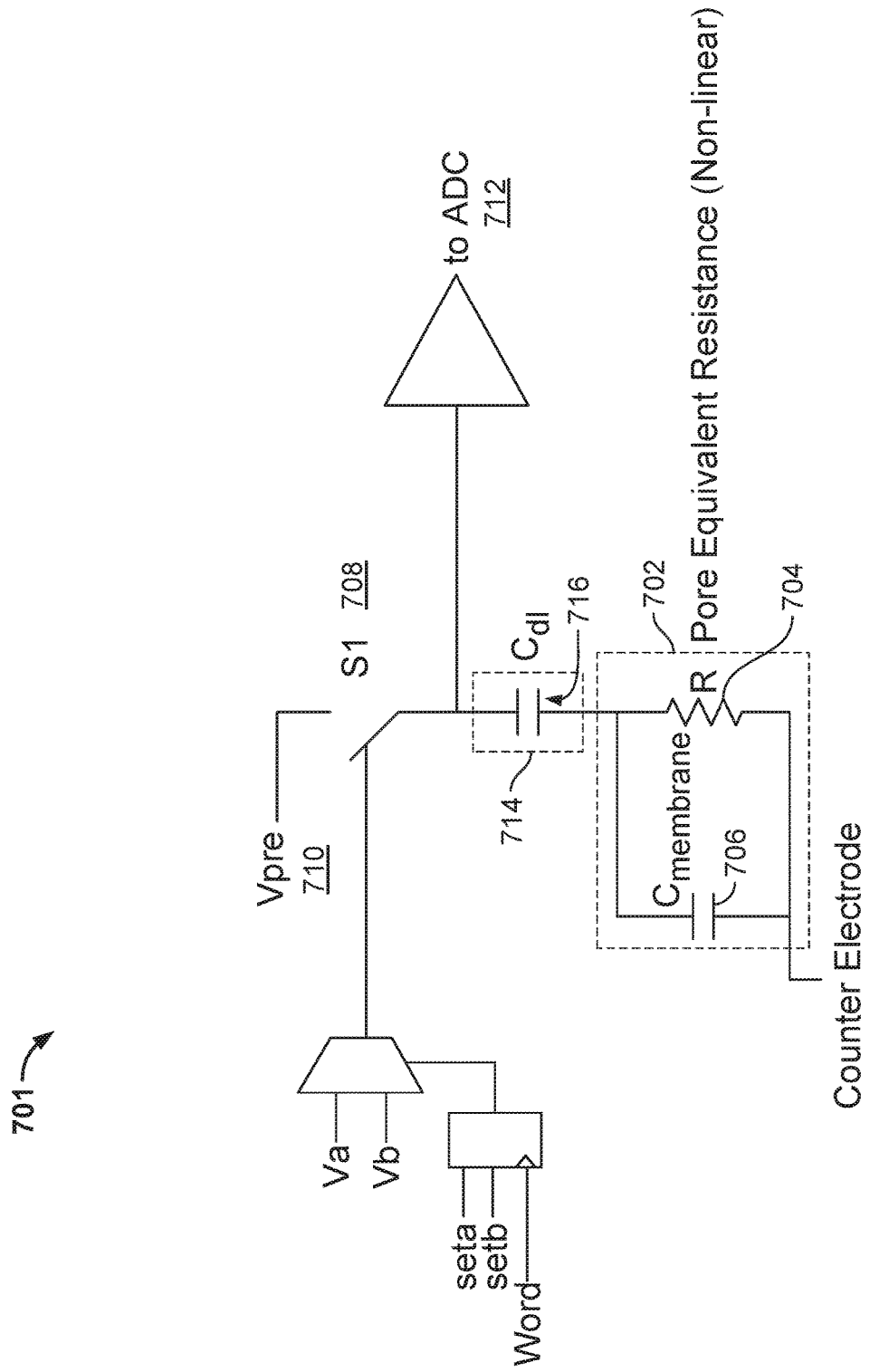
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane and an electrical model 714 representing the electrical properties of the working electrode are shown. Electrical model 702 includes a capacitor 706 that models a capacitance associated with the membrane ($C_{membrane}$) and a resistor 704 that models a resistance associated with the nanopore in different states (e.g., the open-channel state or the states corresponding to having different types of tag/molecule inside the nanopore). Electrical model 714 includes a capacitor 716 that models a capacitance associated with the working electrode. The capacitance associated with the working electrode is also referred to as a double layer capacitance ($C_{dl}$). Note in FIGS. 7A and 7B that the respective circuitry does not require an extra capacitor (e.g., $n_{cap}$ 508 in FIG. 5) that is fabricated on-chip, thereby facilitating the reduction in size of the nanopore based sequencing chip.

Figure 8:
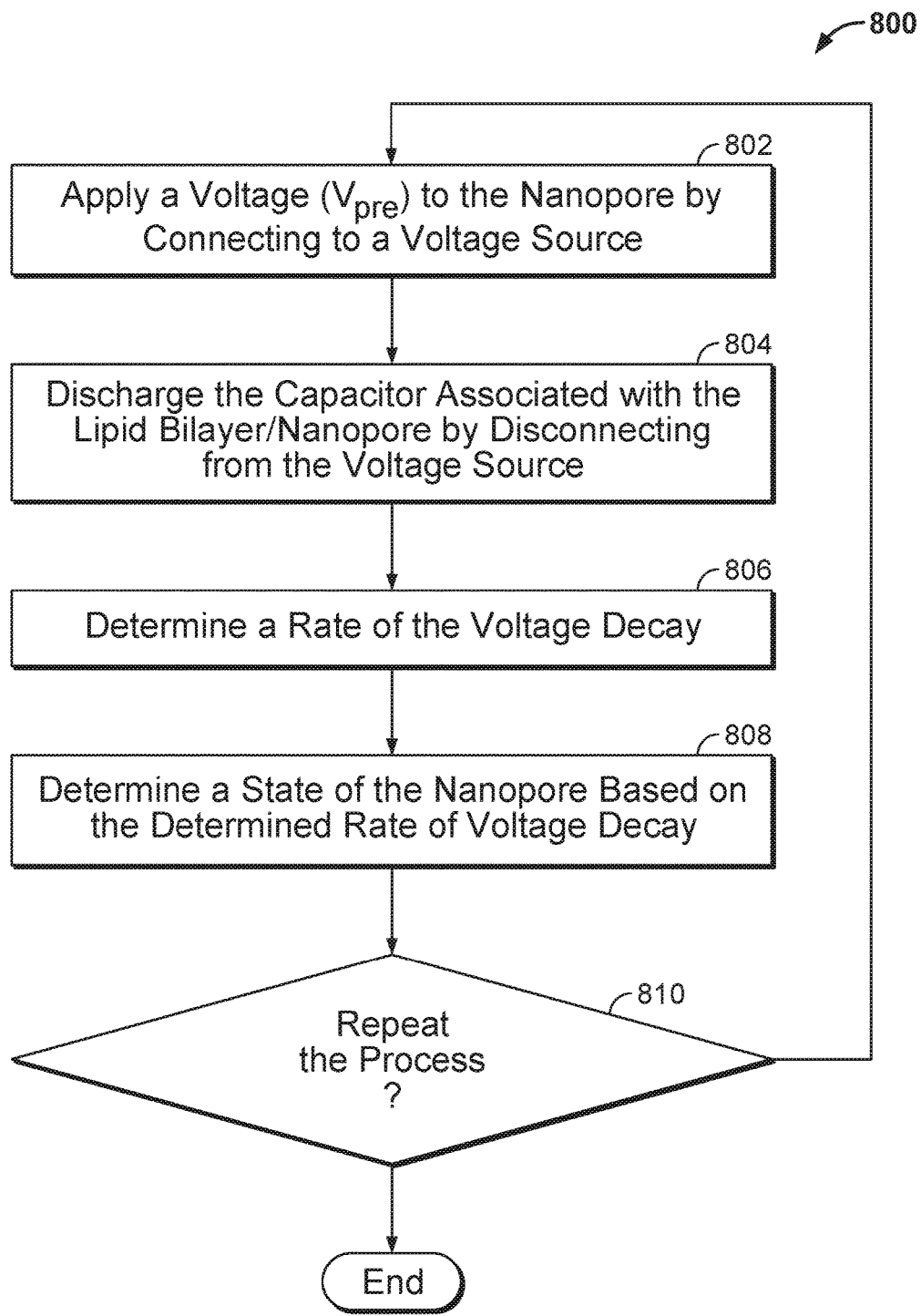
FIG. 8 illustrates an embodiment of a process 800 for analyzing a molecule inside a nanopore, wherein the nanopore is inserted in a membrane.
Figure 9:
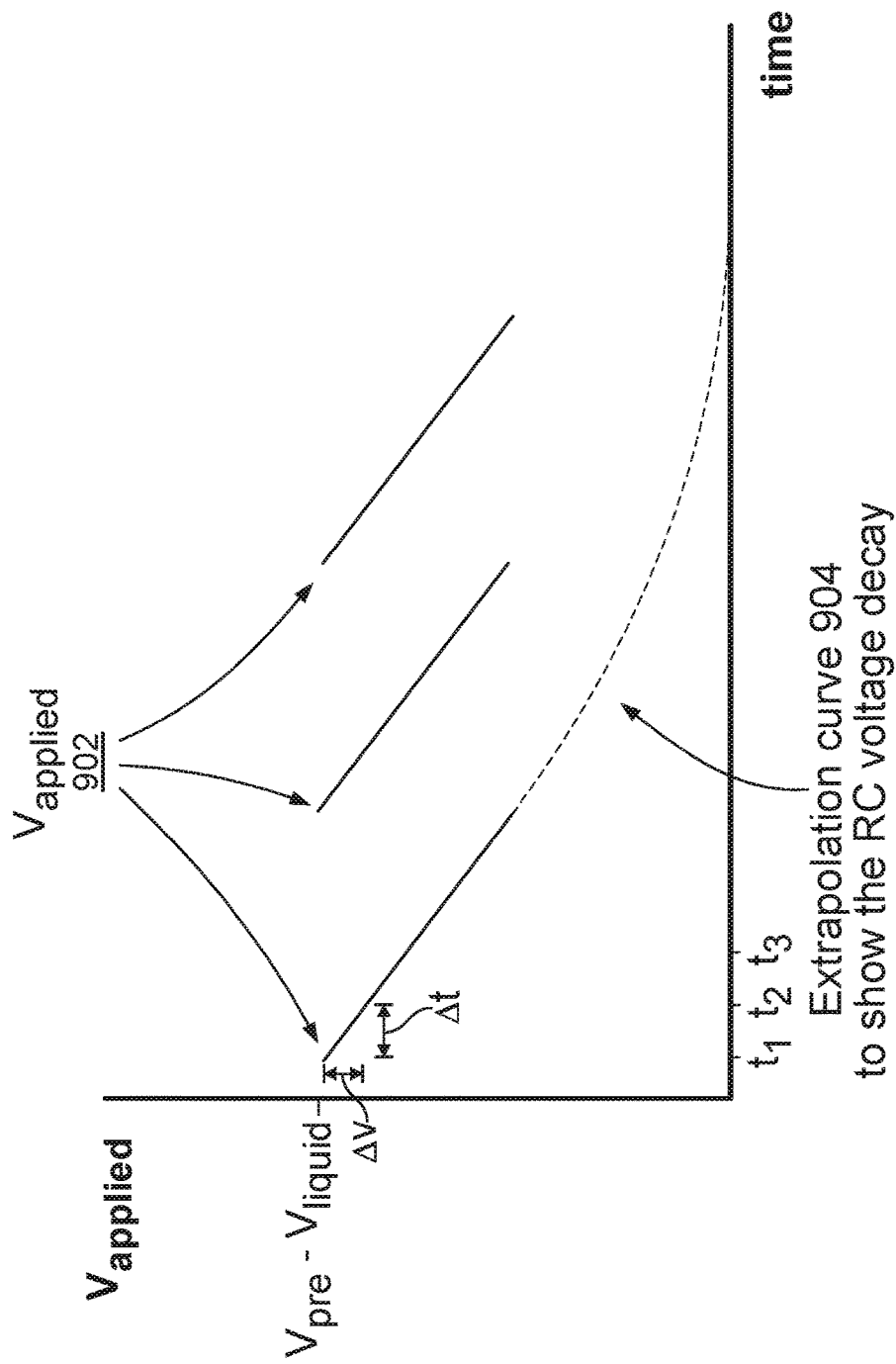
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. The voltage across the nanopore changes over time. The rate of the voltage decay (i.e., the steepness of the slope of the voltage across the nanopore versus time plot) depends on the cell resistance (e.g., the resistance of resistor 704 in FIG. 7A). More particularly, as the resistances associated with the nanopore in different states (e.g., the open-channel state, the states corresponding to having different types of molecules inside the nanopore are different due to the molecules' distinct chemical structure, different corresponding rates of voltage decay may be observed and thus may be used to identify the molecule in the nanopore.

Figure 10:
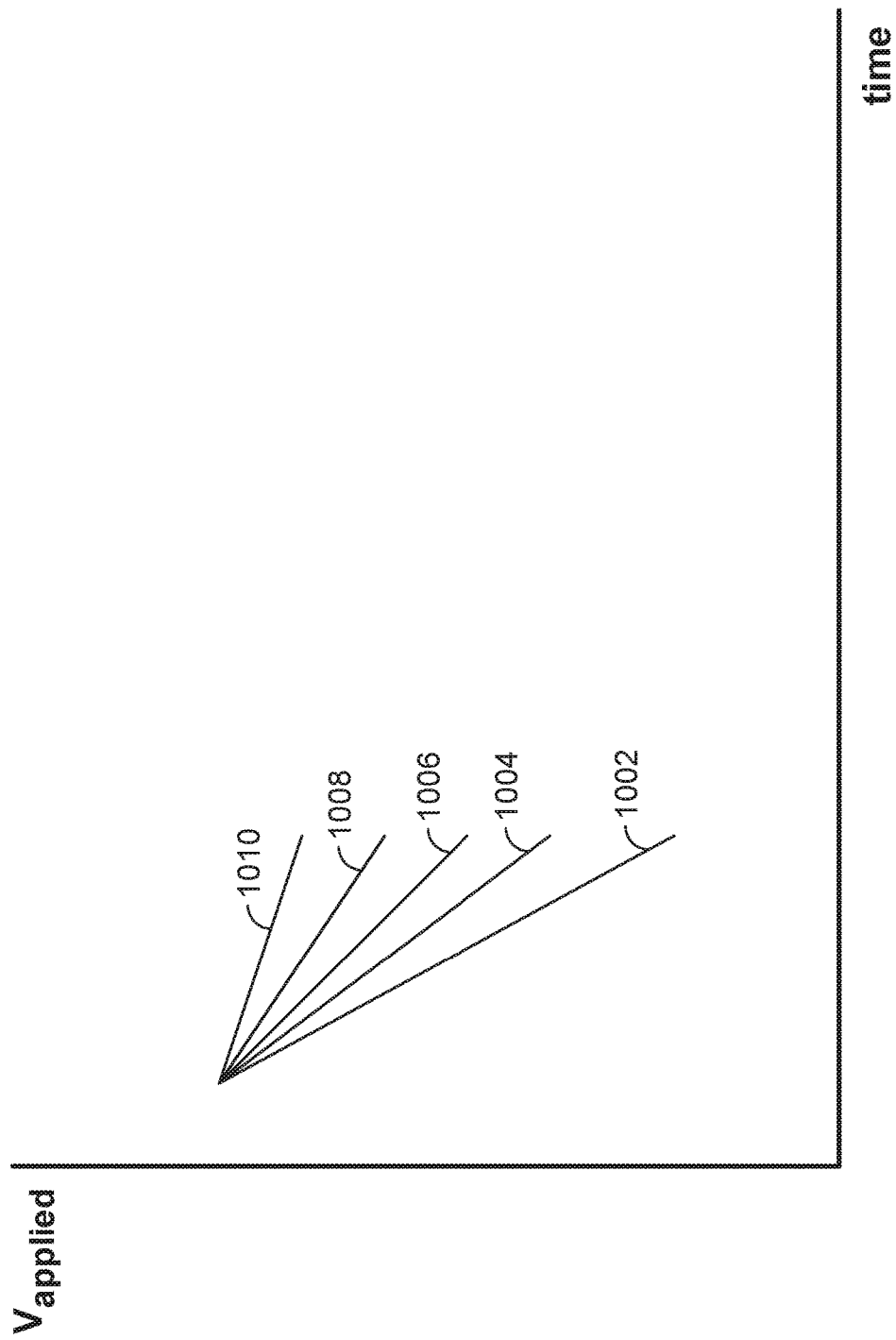
FIG. 10 illustrates an embodiment of the plots of the voltage applied across the nanopore versus time when the nanopore is in different states.

FIG. 10 illustrates an embodiment of the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

Allowing the voltage applied across the nanopore to decay over a time period during which the nanopore is in a particular detectable state has many advantages. One of the advantages is that the elimination of the operational amplifier, the pass device, and the capacitor (e.g., $n_{cap}$ 508 in FIG. 5) that are otherwise fabricated on-chip in the cell circuitry significantly reduces the footprint of a single cell in the nanopore based sequencing chip, thereby facilitating the scaling of the nanopore based sequencing chip to include more and more cells (e.g., having millions of cells in a nanopore based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to create the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. For example, they can be used to correct for baseline drift arising from AC-non-faradaic operation.

The ratio of the capacitance associated with the membrane (see $C_{membrane}$ 706 of FIGS. 7A and 7B) and the capacitance associated with the working electrode (see $C_{dl}$ 716 of FIGS. 7A and 7B) may be adjusted to achieve optimal overall system performance. For example, increased system performance may be achieved by reducing $C_{membrane}$ while maximizing $C_{dl}$. In another example, $C_{membrane}$ is adjusted to create the required RC time constant without the need for additional on-chip capacitance, thereby allowing a significant reduction in cell size and chip size. In another example, $C_{dl}$ is maximized such that the impedance associated with $C_{dl}$ is close to an AC (alternating current) short circuit compared with the impedance associated with $C_{membrane}$.

Figure 11:
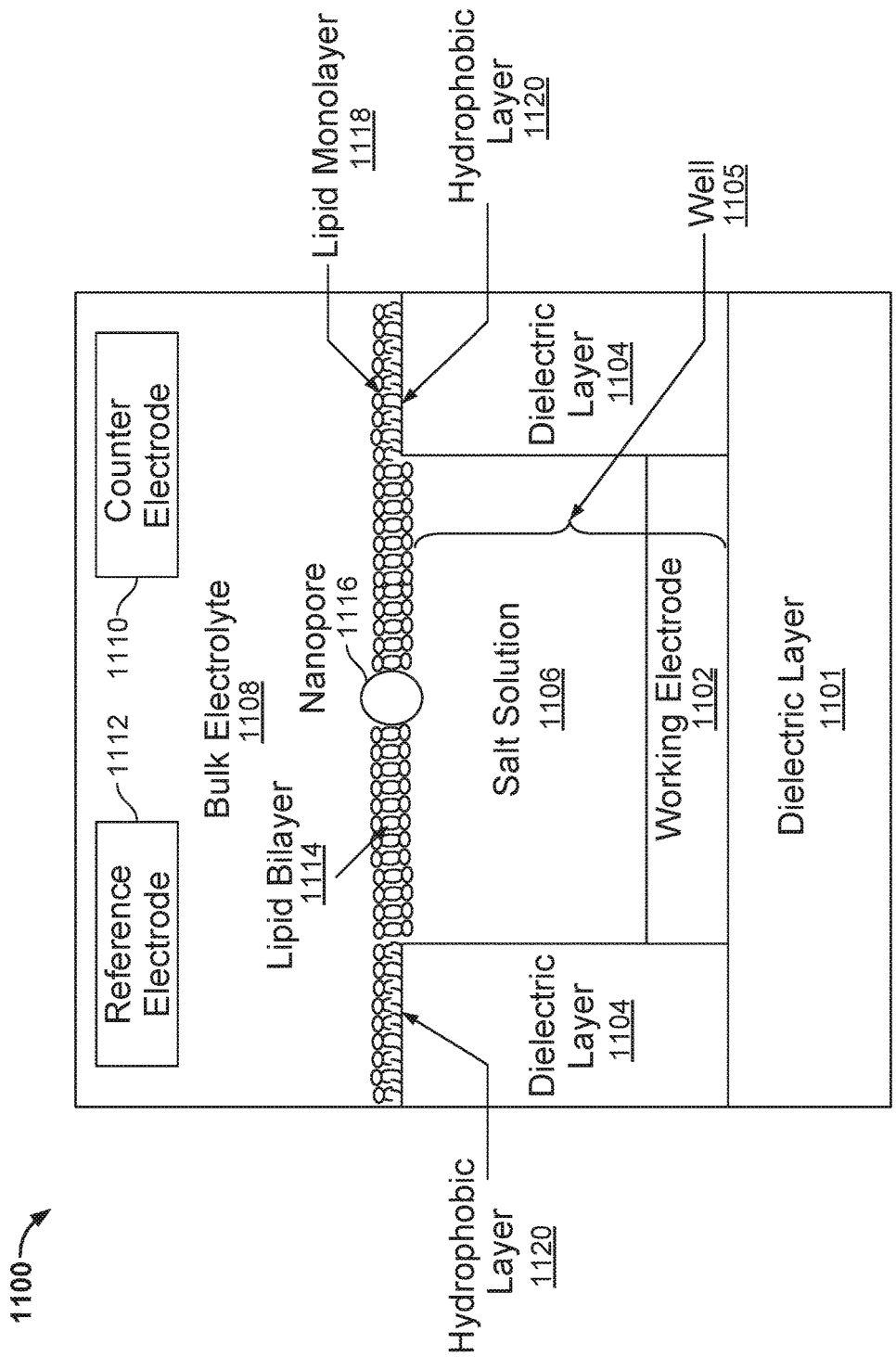
FIG. 11 illustrates an embodiment of a cell 1100 in a nanopore based sequencing chip.

FIG. 11 illustrates an embodiment of a cell 1100 in a nanopore based sequencing chip. In this embodiment, the ratio of the $C_{membrane}$ and $C_{dl}$ may be adjusted by increasing $C_{dl}$, as will be described in greater detail below.

Cell 1100 includes a dielectric layer 1101. Dielectric material used to form dielectric layer 1101 includes glass, oxides, nitrides, and the like. Cell 1100 further includes a dielectric layer 1104 above dielectric layer 1101. Dielectric layer 1104 forms the walls surrounding a well 1105 in which a working electrode 1102 is located at the bottom. Dielectric material used to form dielectric layer 1104 includes glass, oxide, silicon mononitride (SiN), and the like. The top surface of dielectric layer 1104 may be silanized. Silanization forms a hydrophobic layer 1120 above the top surface of dielectric layer 1104. In some embodiments, hydrophobic layer 1120 has a thickness of about 1.5 nanometer (nm).

Well 1105 formed by the dielectric layer walls 1104 further includes a film of salt solution 1106 above working electrode 1102. Salt solution 1106 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the film of salt solution 1106 has a thickness of about three microns (μm).

As shown in FIG. 11, a membrane is formed on top of dielectric layer 1104 and spans across well 1105. For example, the membrane includes a lipid monolayer 1118 formed on top of hydrophobic layer 1120. As the membrane reaches the opening of well 1105, the lipid monolayer transitions to a lipid bilayer 1114 that spans across the opening of the well. A bulk electrolyte 1108 containing protein nanopore transmembrane molecular complexes (PNTMC) and the analyte of interest is placed directly above the well. A single PNTMC/nanopore 1116 is inserted into lipid bilayer 1114 by electroporation. Nanopore 1116 crosses lipid bilayer 1114 and provides the only path for ionic flow from bulk electrolyte 1108 to working electrode 1102. Bulk electrolyte 1108 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Cell 1100 includes a counter electrode (CE) 1110, which is an electrochemical potential sensor. Cell 1100 also includes a reference electrode 1112. In some embodiments, counter electrode 1110 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 1102 is a metal electrode. For non-faradaic conduction, working electrode 1102 may be made of metals that are resistant to corrosion and oxidation, e.g., platinum, gold, titanium nitride and graphite. For example, working electrode 1102 may be a platinum electrode with electroplated platinum.

As discussed above, the ratio of $C_{membrane}$ and $C_{dl}$ in cell 1100 may be adjusted by increasing $C_{dl}$. The double layer capacitance ($C_{dl}$) associated with working electrode 1102 may be increased by increasing the thickness of working electrode 1102. In some embodiments, the thickness of working electrode 1102 ranges from 10 nanometers to 1 micron.

$C_{dl}$ may also be increased by maximizing the surface area of working electrode 1102 for a given volume. As the surface area increases, the capacitance of the double layer ($C_{dl}$) increases, and a greater amount of ions can be displaced with the same applied potential before the capacitor becomes charged. For example, the surface area of the working electrode may be increased by making the electrode "spongy." In some embodiments, the capacitance of the double layer can be enhanced by electroplating platinum metal onto a 5 micron diameter smooth platinum electrode in the presence of a detergent. The detergent creates nanoscale interstitial spaces in the platinum metal, making it "spongy." The platinum sponge soaks up electrolyte and creates a large effective surface area (e.g., 33 pF per square micron of electrode top-down area).

Another way to increase $C_{dl}$ is by increasing the base surface area of working electrode 1102. For example, if the working electrode has a cylindrical shape, then the base surface area of the cylinder may be increased. In another example, if the working electrode has a rectangular prism shape, then the base surface area of the rectangular prism may be increased. However, cell 1100 has a drawback. Working electrode 1102 and lipid bilayer 1114 have the same (or similar) base surface area or cross sectional area. When the base surface area of working electrode 1102 is increased, the base surface area of the opening of well 1105 and lipid bilayer 1114 are both increased as well. As a result, both $C_{membrane}$ and $C_{dl}$ are increased simultaneously. In other words, to optimize the overall system performance, $C_{membrane}$ cannot be reduced while maximizing $C_{dl}$ by adjusting the base area of well 1105 alone.

Figure 12:
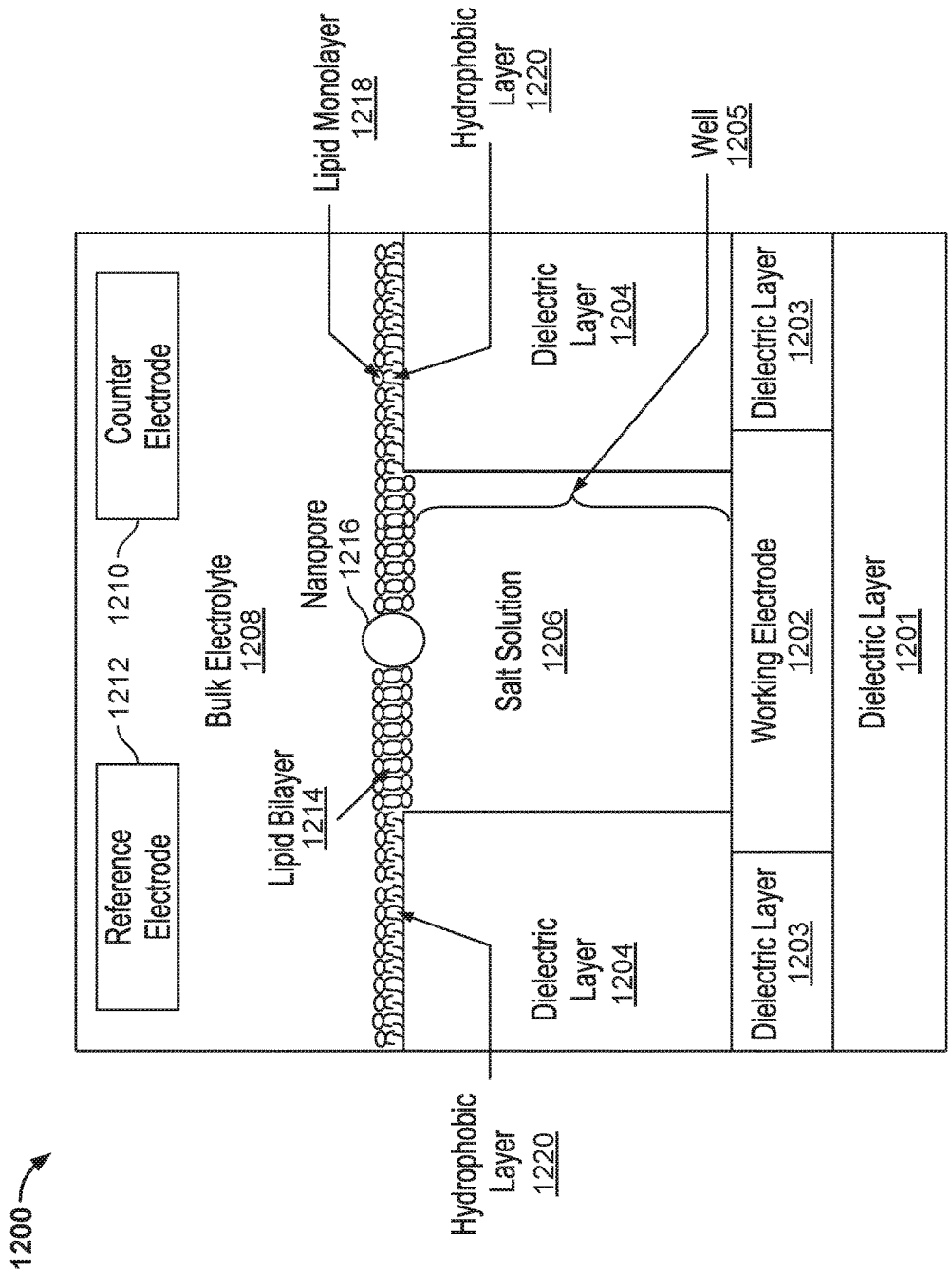
FIG. 12 illustrates an embodiment of a cell 1200 in a nanopore based sequencing chip.

FIG. 12 illustrates an embodiment of a cell 1200 in a nanopore based sequencing chip. In contrast to cell 1100, $C_{membrane}$ and $C_{dl}$ in cell 1200 may be adjusted independently by adjusting the base surface area of the membrane and the base surface area of the working electrode separately.

Cell 1200 includes a dielectric layer 1201. Cell 1200 further includes a working electrode 1202 and a dielectric layer 1203 above dielectric layer 1201. In some embodiments, working electrode 1202 is circular in shape and dielectric layer 1203 forms the walls surrounding working electrode 1202. Cell 1200 further includes a dielectric layer 1204 above working electrode 1202 and dielectric layer 1203. Dielectric layer 1204 forms the walls surrounding a well 1205. In some embodiments, dielectric layer 1203 and dielectric layer 1204 together form a single piece of dielectric. Dielectric layer 1203 is the portion that is disposed horizontally adjacent to working electrode 1202, and dielectric layer 1204 is the portion that is disposed above and covering a portion of the working electrode. The dielectric forms well 1205, which has an opening above an uncovered portion of the working electrode. In some embodiments, dielectric layer 1203 and dielectric layer 1204 are separate pieces of dielectric and they may be grown separately.

Inside well 1205, a film of salt solution 1206 is deposited above working electrode 1202. Salt solution 1206 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the film of salt solution 1206 has a thickness of about three microns. The thickness of the film of salt solution 1206 may range from 0-5 microns.

Dielectric material used to form dielectric layers 1201, 1203, and 1204 includes glass, oxide, silicon mononitride (SiN), and the like. The top surface of dielectric layer 1204 may be silanized. Silanization forms a hydrophobic layer 1220 above the top surface of dielectric layer 1204. In some embodiments, hydrophobic layer 1220 has a thickness of about 1.5 nanometer (nm).

As shown in FIG. 12, a membrane is formed on top of dielectric layer 1204 and spans across well 1205. For example, the membrane includes a lipid monolayer 1218 formed on top of hydrophobic layer 1220 and as the membrane reaches the opening of well 1205, the lipid monolayer transitions to a lipid bilayer 1214 that spans across the opening of the well. Hydrophobic layer 1220 facilitates the formation of lipid monolayer 1218 above dielectric layer 1204 and the transition from a lipid monolayer to a lipid bilayer. A bulk electrolyte 1208 containing protein nanopore transmembrane molecular complexes (PNTMC) and the analyte of interest is placed directly above the well. A single PNTMC/nanopore 1216 is inserted into lipid bilayer 1214 by electroporation. Nanopore 1216 crosses lipid bilayer 1214 and provides the only path for ionic flow from bulk electrolyte 1208 to working electrode 1202. Bulk electrolyte 1208 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

In cell 1200, the base surface area of the opening of well 1205 (which is the same as the base surface area of lipid bilayer 1214) and the base surface area of working electrode 1202 are determined by the dimensions of dielectric layer 1204 and dielectric layer 1203, respectively. The base surface area of working electrode 1202 is greater than or equal to the base surface area of the opening of well 1205.

Cell 1200 includes a counter electrode (CE) 1210, which is an electrochemical potential sensor. Cell 1200 also includes a reference electrode 1212. In some embodiments, counter electrode 1210 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 1202 is a metal electrode. For non-faradaic conduction, working electrode 1202 may be made of metals that are resistant to corrosion and oxidation, e.g., platinum, gold, titanium nitride and graphite. For example, working electrode 1202 may be a platinum electrode with electroplated platinum.

Similar to cell 1100, the ratio of $C_{membrane}$ and $C_{dl}$ in cell 1200 may be adjusted by increasing $C_{dl}$. The double layer capacitance ($C_{dl}$) associated with working electrode 1202 may be increased by increasing the thickness of working electrode 1202. In some embodiments, the thickness of working electrode 1202 ranges from 10 nanometers to 1 micron.

$C_{dl}$ may also be increased by maximizing the surface area of working electrode 1202 for a given volume. For example, the surface area of the working electrode may be increased by making the electrode "spongy." In some embodiments, the capacitance of the double layer can be enhanced by electroplating platinum metal onto a 5 micron diameter smooth platinum electrode in the presence of a detergent.

Another way to adjust the ratio of $C_{membrane}$ and $C_{dl}$ is by adjusting the base surface area of the opening of well 1205 and the base surface area of working electrode 1202 independently from each other. In cell 1200, the base surface area of the opening of well 1205 (which is the same as the base surface area of lipid bilayer 1214) and the base surface area of working electrode 1202 are determined by the dimensions of dielectric layer 1204 and dielectric layer 1203, respectively. Therefore, the two base surface areas may be optimized independently to provide the desired ratio between $C_{membrane}$ and $C_{dl}$. For example, as shown in FIG. 12, the base surface area of working electrode 1202 is kept at the same size as working electrode 1102 in FIG. 11, while the base surface area of the opening of well 1205 is reduced, thereby reducing $C_{membrane}$, while maximizing $C_{dl}$.

In some embodiments, the diameters of working electrode 1202 and the opening of well 1205 range from 0.5 to 6 microns. $C_{membrane}$ has a capacitance that ranges from 5 to 300 femto farad (fF).

FIG. 13 illustrates an embodiment of a process for constructing a cell in a nanopore based sequencing chip, wherein $C_{membrane}$ and $C_{dl}$ in the cell may be adjusted independently by adjusting the base surface area of the membrane and the base surface area of the working electrode separately. At step A, a layer of dielectric 1 is disposed on top of a metal 6 layer (M6). In some embodiments, the layer of dielectric 1 has a thickness of about 400 nm. At step B, the layer of dielectric 1 is etched to create a well. At step C, a layer of metal or metal oxide is deposited to fill the well created at step B. At step D, the excess metal or metal oxide is removed. For example, the excess metal or metal oxide may be removed using chemical mechanical polishing (CMP) techniques. The remaining metal or metal oxide deposited in the well forms a working electrode. After the working electrode is formed, a layer of dielectric 2 is deposited on top of the dielectric 1 and the working electrode. At step E, the layer of dielectric 2 is etched to create a well exposing only a portion of the upper base surface area of the working electrode. Because the base surface area of the opening of the well is independent from the base surface area of the working electrode, $C_{membrane}$ and $C_{dl}$ in the cell may be fine tuned to obtain the desired $C_{membrane}$ and $C_{dl}$ ratio.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A nanopore sequencing device, comprising:
 a working electrode; and
 a dielectric layer, wherein a portion of the dielectric layer is disposed above and covering a portion of the working electrode, and wherein the dielectric layer forms a surrounding side wall of a well, wherein the well has an opening above an uncovered portion of the working electrode; and
 wherein the dielectric layer comprises a top surface, and wherein a membrane may form on top of the top surface and span across the opening of the well above the uncovered portion of the working electrode; and
 wherein a base surface area of the working electrode is greater than a base surface area of the opening above the uncovered portion of the working electrode.

2. The nanopore sequencing device of claim 1, wherein the dielectric layer comprises a first dielectric layer and a second dielectric layer, and wherein the first dielectric layer corresponds to a portion of the dielectric layer disposed horizontally adjacent to the working electrode and the second dielectric layer corresponds to the portion of the dielectric layer disposed above and covering a portion of the working electrode.

3. The nanopore sequencing device of claim 1, wherein the base surface area of the working electrode and the base surface area of the opening are selected based on a ratio of a capacitance associated with the working electrode and a capacitance associated with a membrane that spans across the opening.

4. The nanopore sequencing device of claim 1, wherein the base surface area of the working electrode is selected based on a desired impedance associated with the working electrode.

5. The nanopore sequencing device of claim 4, wherein the desired impedance is substantially equivalent to an alternating current (AC) short circuit at an operating frequency.

6. The nanopore sequencing device of claim 1, wherein the base surface area of the working electrode, the thickness of the working electrode, and the surface area per volume of the working electrode are selected based on a desired capacitance associated with the working electrode.

7. The nanopore sequencing device of claim 1, wherein the base surface area of the opening is selected based on a desired RC time constant, and wherein the desired RC time constant comprises a resistance associated with a nanopore inserted in a membrane that spans across the opening and a capacitance associated with the membrane that spans across the opening.

8. The nanopore sequencing device of claim 1, further comprising a hydrophobic layer formed above the top surface of the dielectric layer and surrounding the opening, wherein the hydrophobic layer facilitates formation of a lipid monolayer on the hydrophobic layer and facilitates formation of a lipid bilayer that spans across the opening.

9. The nanopore sequencing device of claim 8, wherein the hydrophobic layer is formed by silanization.

10. The nanopore sequencing device of claim 1, wherein the dielectric layer is formed using one of the following: glass, oxides, and nitrides.

11. The method of constructing a nanopore sequencing device, comprising:
constructing a working electrode; and
constructing a dielectric layer, wherein a portion of the dielectric layer is disposed above and covering a portion of the working electrode, and wherein the dielectric layer forms a surrounding side wall of a well, wherein the well has an opening above an uncovered portion of the working electrode; and
wherein the dielectric layer comprises a top surface, and wherein a membrane may form on top of the top surface and span across the opening of the well above the uncovered portion of the working electrode; and
wherein a base surface area of the working electrode is greater than a base surface area of the opening above the uncovered portion of the working electrode.

12. The method of claim 11, wherein the dielectric layer comprises a first dielectric layer and a second dielectric layer, and wherein the first dielectric layer corresponds to a portion of the dielectric layer disposed horizontally adjacent to the working electrode and the second dielectric layer corresponds to the portion of the dielectric layer disposed above and covering a portion of the working electrode.

13. The method of claim 11, further comprising: selecting the base surface area of the working electrode and the base surface area of the opening based on a ratio of a capacitance associated with the working electrode and a capacitance associated with a membrane that spans across the opening.

14. The method of claim 11, further comprising selecting the base surface area of the working electrode based on a desired impedance associated with the working electrode.

15. The method of claim 14, wherein the desired impedance is substantially equivalent to an alternating current (AC) short circuit at an operating frequency.

16. The method of claim 11, further comprising selecting the base surface area of the working electrode, the thickness of the working electrode, and the surface area per volume of the working electrode based on a desired capacitance associated with the working electrode.

17. The method of claim 11, further comprising selecting the base surface area of the opening based on a desired RC time constant, and wherein the desired RC time constant comprises a resistance associated with a nanopore inserted in a membrane that spans across the opening and a capacitance associated with the membrane that spans across the opening.

18. The method of claim 11, further comprising forming a hydrophobic layer above the top surface of the dielectric layer and surrounding the opening, the hydrophobic layer facilitates formation of a lipid monolayer on the hydrophobic layer and facilitates formation of a lipid bilayer that spans across the opening.

19. The method of claim 18, wherein the hydrophobic layer is formed by silanization.

20. The method of claim 11, wherein the dielectric layer is formed using one of the following: glass, oxides, and nitrides.

* * * * *